United States Patent [19]

Hutterer

[11] Patent Number: 4,837,219

[45] Date of Patent: Jun. 6, 1989

[54] MEDICATION FOR ALZHEIMER'S DISEASE

[76] Inventor: Jeffrey Hutterer, 67-35 Harrow St., Forest Hills, N.Y. 11375

[21] Appl. No.: 116,916

[22] Filed: Nov. 5, 1987

[51] Int. Cl.$^4$ .................. A61K 31/195; A61K 31/415
[52] U.S. Cl. ..................................... 514/400; 514/561
[58] Field of Search ................................ 514/400, 561

[56] References Cited

PUBLICATIONS

Chem.-Abst. 77 (1972)-150796t.

Primary Examiner—Stanley J. Friedman
Attorney, Agent, or Firm—Michael I. Kroll

[57] ABSTRACT

A medication for Alzheimer's disease is provided and consists of six ingredients mixed into fruit juice, to bring about improvements in an Alzheimer's disease patient. The ingredients are Choline (from Choline Bitartrate), L-Tyrosine, L-Phenylalanime, L-Leucine, Zinc (from Zinc Gluconate) and Copper (from Copper Gluconate).

1 Claim, No Drawings

MEDICATION FOR ALZHEIMER'S DISEASE

BACKGROUND OF THE INVENTION

1. Field of the Invention

The instant invention relates generally to Alzheimer's disease and more specifically it relates to a medication for Alzheimer's disease.

Today many scientists seem confident that the destruction of brain cells in victims of Alzheimer's disease is produced by a breakdown in the chemical circuits of the brain. What they are not sure about is the underlying cause of this breakdown.

There are two different kinds of cells in the brains of humans and other animals. One kind is the neuron, or nerve cell, usually made up of a cell body, many branching dendrites, and a long, tail-like axon that ends in a cluster of terminal branches. Neurons are the "thinking" cells of the brain, the ones that control all memories, throughts, feelings and actions. They are also the cells damaged by Alzheimer's disease. Surrounding the neurons are billions of glial cells; they form a "glue" that supports the nerve cells and provides them with nourishment.

It has been estimated that the human brain contains at least ten billion individual neurons. The amazing way in which these cells communicate with each other and with the neurons of the body's nervous system is one of the great discoveries of modern brain research.

Scientists have known for many years that the brain's communication system used electrical impulses in some way. An electroencephalogram records and measures the waves of electrical energy that move constantly through a normal brain. It was only recently, however, that researchers learned about the role that chemicals play in connecting neurons with each other.

The brain and nervous system use both electricity and chemistry to transmit information, send commands and perform all their other complex functions. The communication system works in this way: Information picked up by one of the body's sense organs is received by a neuron in the form of an electrical impulse. This impulse moves through the neuron's cell body and down the long axon. The axon's terminal branches are positioned close to but not quite touching the dendrites or body of at least one other nerve cell. The tiny space between the two cells, called a synaptic cleft, can be crossed only by a chemical bridge.

When the electrical impulse reaches the end of the axon, it triggers the release of chemicals known as neurotransmitters. The neurotransmitters move across the synaptic cleft and lock into special receptors located on the surface of the other neuron. Once it is received by the receptors, the chemical message is changed back into an electrical impulse, which is then transmitted to other neurons in the same manner.

By means of this unique communication system, the billions of neurons in the brain are connected to each other through amazingly complex pathways, or circuits. One neuron alone may be in touch with the axons or dendrites of one thousand other neurons and be able to receive messages from thousands more. These connected neurons work together in receiving and interpreting information, in controlling the actions of the body, in storing memories. Because of the brain's neuron circuits, human beings are able to solve complicated problems, create great works of art, or construct elaborate plans for the future using millions of isolated pieces of information.

In recent years, scientists have discovered that all the neurons connected in a circuit usually produce and respond to the same kinds of neurotransmitters. Researchers have succeeded in isolating and identifying some of these chemical messengers, among them acetylcholine, norepinephrine, serotonin and dopamine. This information is not only of vital importance to brain research but has also been of great help in studying illnesses that affect nerve cells.

2. Description of the Prior Art

A conventional treatment for Alzheimer's disease is the use of drugs to expand blood vessels, so that they can carry more blood to the brain. Such drugs are called vasodilators and accordingly, some relief of confusion and improvement in mental alertness and memory have resulted from their use. Though some patients have reportedly benefited from these drugs, becoming less confused and more alert, the benefits have not always correlated with increased blood flow. Dilation, therefore, may not be the major effect of some vasodilatiors. Some may improve the brain's use of oxygen and nutrients, and some perhaps help restore the proper chemical balance.

One major breakthrough has already been made in the treatment of Parkinson's disease, a nerve ailment causing loss of muscle control. Studies have shown that this disease is a result of damage in some of the dopaminergic brain circuits—that use dopamine as a neurotransmitter. The symptoms of Parkinson's disease can be relieved by giving the patient drugs that replace the lost dopamine in the brain cells. Patients with Parkinson's disease have been treated successfully with L-dopa, a drug which is converted in the body into a neurotransmitter. Accordingly it is possible that the same drug may be used to help patients with other forms of dementia, but the results of research in this area indicate that it will be a long time before failing mental powers can be restored by this treatment.

About twenty percent of patients who were given a drug called dihydroergotozine mesylate, sold as Hydergine, showed some improvement. It is said to work better in preventing mild dementia from getting worse than in more advanced cases and not all doctors will prescribe this drug. Drugs that bind aluminum, to eliminate that metal from the blood are also being tried.

It has been found that vasopressin, a pituitary hormone, affects memory. This drug is being tested on patients and it is given as an inhalant, as there is evidence that nerve endings which are sensitive to smell may pick it up and carry it to the brain. Investigators have used it in experiments involving rats. If the rats made a wrong turn in a smple T-shaped maze, the rats were given a mild electric shock. When they were given injections of vasopressin, either before or shortly after they explored the maze, their memories improved. When they were retested up to forty eight or seventy two hours after the first trial, many of the rats treated with vasopressin avoided the shock, while the untreated rats usually forgot which side of the maze was associated with the shock after twenty four hours. Studies have indicated that Alzheimer's disease could also be related to problems in the brain's chemical circuits. Scientists have found at least two chemical circuits that are abnormal in Alzheimer's victims. The most important is the cholingergic circuit, which uses acetylcholine as its primary neurotransmitter. One of the main centers of cholinergic cells in the brain is an area known as the nucleus basilis. The cells in this region produce large amounts of acetylcholine and use it in transmitting messages to other circuits of neurons. Tests on the brains of people who have had Alzheimer's disease show that they have abnormally low amounts of acetyloholine in the nucleus basilis. There also seems to be a shortage of the enzymes that produce the chemical. The cholinergic cells in the nucleus basilis have connections to many parts of the brain, including the limbic system and the frontal and parietal lobes of the cortex. Many researchers suspect that the shortage of acetycholine in the nucleus basilis affects communication among these cells, causing them to develop the lesions of Alzheimer's disease and eventually die.

To test this theory, they have tried to slow the progression of the disease by increasing the amount of acetylcholine in the brains of victims. This is usually done by giving the patients large amounts of lecithin, a substance containing choline, one of the essential components of acetylcholine. The other component, acetyl, is found naturally in the brain. A "memory pill" containing lecithin, a substance commonly found in many foods, once showed promise of producing a revival of memory in dementia patients, but a report maintains that the drug is ineffective. Researchers have tried feeding pure lecithin to senile patients and to healthy ones, to see if memory improved, but so far the improvement has not been marked.

A drug called physostigmine keeps acetylcholine from rapidly breaking down after it is released from nerve cells. There is evidence that this drug helps, but there are unpleasant side effects. So far these tests have not produced any significant results, although some slight improvement has been seen in a few of the people treated. It may be that there are simply not enough processing enzymes available to make acetylcholine even when the supply of choline is greatly increased. Further tests are underway using different methods of influencing the chemistry of the cholinergic circuits, and they may prove more successful. Many scientists believe tht such tests and studies hold the most promise for the eventual discovery of an effective treatment for Alzheimer's disease.

SUMMARY OF THE INVENTION

A primary object of the present invention is to provide a medication for Alzheimer's disease that will overcome the shortcomings of the prior art through a more holistic approach which emphasizes the interaction of nutrients.

Another object is to provide a medication for Alzheimer's disease that is composed of nutrients combined with choline, in order to help unleash its trapped potential within the brain and further hope that these facilitating substances might also be potentiated by the choline and/or diminish the Alzheimer symptoms through their own biochemical actions.

An additional object is to provide a medication for Alzheimer's disease composed of six ingredients which will bring about dramatic improvements in an Alzheimer's disease patient, such as a decrease in psychomotor agitation, confusion and disorientation, lessening of anxiety, depression and regressive behaviors, improved bladder and bowel control, enhanced short-term memory and greater clarity in verbal communication.

A further object is to provide a medication for Alzheimer's disease that is simple and easy to use.

A still further object is to provide a medication for Alzheimer's disease that is economical in cost to manufacture.

Further objects of the invention will appear as the description proceeds.

To the accomplishment of the above and related objects, attention being called to the fact, that changes may be made in the specific construction described within the scope of the appended claims.

DETAILED DESCRIPTION OF THE PREFERRED EMBODIMENTS

A detailed description will hereinafter be given of the present invention being a medication for Alzheimer's disease which consists of 300 milligrams of Choline(-from Choline Bitartrate), 100 milligrams of L-Tyrosine, 100 milligrams of L-Phenylalanine 50 milligrams of L-Leucine, 15 milligrams of Zinc (from Zinc Gluconate) and 2 milligrams Copper (from Copper Gluconate). (These are the suggested dosages for advanced cases of the disease. Less seriously ill patients may require less medication.)

To administer the medication for Alzheimer's disease the following steps are taken:

1. All six ingredients to an eight ounce glass of any fruit juice for palatability.
2. Allow the mixture to stand for two hours, in order for the tablets and powders to dissolve and for some pre-digestion to occur.
3. Stir the formula in a blender just prior to ingestion for optimum homogenization.
4. Give half a cup of the formula in the morning following breakfast to a person with Alzheimer's disease to drink.
5. Give the other half a cup of the formula after dinner to the person with Alzheimer's disease to drink.

Amelioration of symptoms will occur within one hour and apparently endure as long as the formula is taken. When treatment is suspended, deterioration is resumed within seventy two hours. The positive changes are, decrease in psychomotor agitation, confusion and disorientation, lessening of anxiety, depression and regressive behaviors, improved bladder and bowel control, enhanced short-term memory and greater clarity in verbal communication.

It will be understood that each of the elements described above, or two or more together, may also find a useful application in other types of methods differing from the type described above.

While certain novel features of this invention have been described and are pointed out in the annexed claims, it is not intended to be limited to the details above, since it will be understood that various omissions, modifications, substitutions and changes in the forms and details of the invention and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A method of preparing and administering a medication for the treatment of Alzheimer's disease which comprises:
   (a) adding 300 milligrams of Choline (from Choline Bitartrate), 100 milligrams of L-Tyrosone, 100 milligrams of L-Phenylalanine, 50 milligrams of L-Leucine, 15 milligrams of Zinc (from Zinc Gluconate) and 2 milligrams Copper (from Copper Gluconate) to an eight ounce glass of any fruit juice for patatibility;
   (b) allowing the mixture to stand for two hours, in order for the tablets and powders to dissolve and for some pre-digestion to occur;
   (c) stirring the formula in a blender just prior to ingestion for optimum homogenization;
   (d) giving half a cup of the formula in the morning following breakfast to a person with Alzheimer's disease to drink; and
   (e) giving the other half a cup of the formula after dinner to the person with Alzheimer's disease to drink.

* * * * *